(12) United States Patent
Vogt

(10) Patent No.: US 9,700,649 B2
(45) Date of Patent: Jul. 11, 2017

(54) POLYMETHYLMETHACRYLATE BONE CEMENT

(71) Applicant: Heraeus Medical GmbH, Wehrheim (DE)

(72) Inventor: Sebastian Vogt, Erfurt (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 102 days.

(21) Appl. No.: 14/672,788

(22) Filed: Mar. 30, 2015

(65) Prior Publication Data

US 2015/0290355 A1  Oct. 15, 2015

(30) Foreign Application Priority Data

Apr. 14, 2014  (DE) .................. 10 2014 105 267

(51) Int. Cl.
*A61L 24/04* (2006.01)
*A61L 27/16* (2006.01)
*A61L 24/06* (2006.01)
*A61L 24/00* (2006.01)

(52) U.S. Cl.
CPC ........... *A61L 24/043* (2013.01); *A61L 24/001* (2013.01); *A61L 24/06* (2013.01); *A61L 27/16* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 5,902,839 | A | 5/1999 | Lautenschlager et al. |
| 8,512,762 | B2 | 8/2013 | Vogt et al. |
| 8,536,243 | B2 | 9/2013 | Leonard et al. |
| 2009/0105144 | A1 | 4/2009 | Vogt et al. |
| 2009/0105366 | A1 | 4/2009 | Vogt et al. |
| 2010/0159027 | A1 | 6/2010 | Vogt et al. |
| 2011/0112210 | A1 | 5/2011 | Vogt et al. |
| 2011/0270259 | A1* | 11/2011 | Shim .................. A61L 24/0015 606/93 |
| 2013/0030058 | A1 | 1/2013 | Vogt et al. |
| 2013/0310466 | A1 | 1/2013 | Vogt |
| 2013/0125786 | A1 | 5/2013 | Vogt |
| 2014/0024739 | A1 | 1/2014 | Vogt |

FOREIGN PATENT DOCUMENTS

| | | |
|---|---|---|
| CN | 1810300 A | 8/2006 |
| DE | 102007052116 A1 | 4/2009 |
| DE | 102007050762 B3 | 5/2009 |
| DE | 102008030312 A1 | 1/2010 |
| DE | 102009005534 B3 | 4/2010 |
| EP | 2 497 502 A2 | 9/2012 |
| EP | 2 550 979 A2 | 1/2013 |
| EP | 2596812 A1 | 5/2013 |
| EP | 2 664 349 A1 | 11/2013 |
| EP | 2 687 239 A2 | 1/2014 |
| JP | 2009-101159 A | 5/2009 |
| JP | 2011-526171 A | 10/2011 |

OTHER PUBLICATIONS

Japanese Office Action for corresponding Japanese Patent Application No. 2015-077479 issued Mar. 29, 2016.
English Translation of Japanese Office Action for corresponding Japanese Patent Application No. 2015-077479 issued Mar. 29, 2016.
European Search Report dated Sep. 4, 2015.
K.-D. Kühn, Up-to-Date Comparison of Physical and Chemical Properties of Commerical Materials: , Springer-Verlag Berlin Heidelberg New York, 2001.
Examination Report dated Nov. 19, 2015.

* cited by examiner

*Primary Examiner* — Robert A Wax
*Assistant Examiner* — Melissa Mercier
(74) *Attorney, Agent, or Firm* — Norris McLaughlin & Marcus P.A.

(57) ABSTRACT

Two-component bone cement comprising A) a paste as component A, comprising a1) methylmethacrylate; a2) at least one methylmethacrylate-soluble polymer having a number average molar mass of less than 500,000 Dalton; a3) at least one methylmethacrylate-insoluble particulate polymer having a particle size D50 of less than 50 μm; a4) at least one methylmethacrylate-soluble hydroperoxide; and a5) at least one methylmethacrylate-soluble tertiary amine; and B) a powder as component B, comprising b1) at least one particulate radiopaquer having a particle size D50 of less than 50 μm; b2) at least one methylmethacrylate-soluble heavy metal salt; and b3) at least one methylmethacrylate-soluble reducing agent.
The mixing of paste A and powdered component B immediately generates a tack-free plastically deformable cement dough, without any waiting time, that self-cures by means of radical polymerization.

9 Claims, No Drawings

POLYMETHYLMETHACRYLATE BONE CEMENT

The invention relates to a two-component polymethylmethacrylate bone cement and to the use thereof.

BACKGROUND OF THE INVENTION

Polymethylmethacrylate bone cements have been in use in medicine for decades for permanent mechanical fixation of total joint endoprostheses. These are based on powder-liquid systems, whereby it is customary to use methylmethacrylate as monomer. A general overview is provided, e.g., in K.-D. Kühn, Knochenzemente für die Endoprothetik: ein aktueller Vergleich der physikalischen and chemischen Eigenschaften handelsüblicher PMMA-Zemente, Springer-Verlag Berlin Heidelberg New York, 2001.

U.S. Pat. No. 8,536,243 B2 describes a powder-gel bone cement system. This concerns a modification of the conventional powder liquid bone cements. The powdered component consists of a polymer, an initiator such as dibenzoylperoxide, and, if applicable, a radiopaquer and hydroxyl apatite. The gel-like component comprises an acrylic monomer such as methylmethacrylate, a radical inhibitor such as hydroquinone, an activator such as N,N-dimethyl-p-toluidine, and a polymer that is dissolved in the acrylic monomer and has a mean molecular weight above 1,000,000 g/mol.

Recently, polymethylmethacrylate bone cements based on the use of cement pastes have also been proposed. DE 102007052116 A1 relates to a one-component bone cement. DE 102007050762 B3 and DE 102008030312 A1 describe two-component bone cements made of two cement pastes that are stored separately in suitable cartridges. The bone cements each contain at least one monomer, suitable polymeric ingredients, and a redox initiator system. In most cases, methylmethacrylate is used as the monomer.

The redox initiator systems used in this context usually consist of peroxides, accelerators and, if applicable, suitable reducing agents. Radicals are formed only if all components of the redox initiator system act in concert. For this reason, the components of the redox initiator system are arranged appropriately in the separate cement pastes such that they cannot trigger a radical polymerisation.

The cement pastes are stable during storage. Only when the two cement pastes are mixed to produce a cement dough, the components of the redox initiator system, previously stored separately in the two pastes, react with each other to form radicals which trigger the radical polymerisation of the monomer that is present. The radical polymerisation then leads to the formation of polymers while consuming the monomer, whereby the cement dough is cured.

It is customary to use static mixers for mixing the cement pastes and to attach them to 2-component cartridges for this purpose. When the two cement pastes are extruded from the cartridges, the two cement pastes are pushed through a static mixer. As a result, the processes of extruding and mixing proceed concurrently. Mixing the cement pastes in the static mixer requires a high extrusion force since the pressure drop at the mixing elements in the static mixer is very high. It is therefore necessary to use powerful pneumatic or mechanical extrusion devices to dispense and mix the cement pastes. Said pneumatic or mechanical extrusion devices are elaborate from a technical point of view and expensive.

An inexpensive option are the manually-operated extrusion guns, which are customary with polymethylmethacrylate bone cements based on powder-liquid systems, which are suitable for said cements, but are not sufficiently powerful for extruding and mixing bone cement pastes through the use of static mixers.

In conventional 2-component cartridges, the volume ratio of paste A to paste B often is 1:1, 1:2, and 1:10. The more the volumes of the pastes to be mixed through the use of static mixers differ, the more difficult it is to generate a homogeneously mix paste. For this reason, very many mixing spirals are needed for large volumes. The larger the number of mixing spirals needed, the larger is the pressure drop in the static mixer during the mixing process. This means that the pastes need to be pressed through the static mixer by a very large force. Due to the nature of manually-operated extrusion devices, the maximally possible extrusion force is limited.

The bone cements usually contain radiopaquer for the cement used in the body to be visible in a radiograph. Common radiopaquers, such as zirconium dioxide and barium sulfate, possess a high density though. Accordingly, if these are present in pastes there is a risk that the radiopaquers sediment which might adversely affect the quality of the cement.

It was the object of the invention to provide a two-component bone cement that overcomes the disadvantages of the prior art described above. Specifically, it shall be feasible to manually mix the two components without using static mixers in order to obtain a cement dough that is tack-free and capable of plastic deformation immediately. Moreover, the nature of the polymethylmethacrylate bone cement to be developed should be such that the radiopaquer is prevented from sedimenting. Any interaction of the monomer with possibly added pharmaceutical agents should also be excluded. Moreover, the components should be simple and inexpensive to manufacture.

The underlying idea of the invention is to develop a polymethylmethacrylate bone cement that allows a pasty component to be manually mixed with a powdered component in appropriate manner such that a self-curing cement dough is generated that can be extruded and applied by means of common, manually-operated cementing devices. The idea is to let the mixing process and the extrusion process of the polymethylmethacrylate bone cement take place one after the other, which is in contrast to two-component polymethylmethacrylate bone cements made up of two pastes, in which the mixing and the application take place concurrently while the two pastes are being extruded through a static mixer. The mixing of two pastes requires the input of a relative large amount of energy. The application of two-component polymethylmethacrylate bone cements therefore necessitates extrusion devices with a high extrusion force.

Surprisingly, it has been evident that it is feasible, by manual mixing of a pasty component, as defined below, with a second powdered component, as defined below, to produce a tack-free plastically deformable bone cement dough that is self-curing by means of radical polymerisation.

SUMMARY OF THE INVENTION

Therefore, the object of the invention was met through a two-component bone cement comprising
A) a paste as component A, comprising
  a1) methylmethacrylate;
  a2) at least one methylmethacrylate-soluble polymer having a number average molar mass of less than 500,000 Dalton;

a3) at least one methylmethacrylate-insoluble particulate polymer having a particle size D50 of less than 50 µm;
a4) at least one methylmethacrylate-soluble hydroperoxide; and
a5) at least one methylmethacrylate-soluble tertiary amine; and B) a powder as component B, comprising
b1) at least one particulate radiopaquer having a particle size D50 of less than 50 µm;
b2) at least one methylmethacrylate-soluble heavy metal salt; and
b3) at least one methylmethacrylate-soluble reducing agent.

After mixing pasty component A and powdered component B, a tack-free plastically deformable cement dough is generated immediately, without any waiting time, that is self-curing by means of radical polymerisation. The two-component bone cement is a polymethylmethacrylate bone cement.

DETAILED DESCRIPTION

One essential advantage of the invention is that the two component cement according to the invention can be stored in and applied from a clearly less expensive cementing system as compared to the known pasty 2-component cements. It is feasible, by means of the two-component bone cement according to the invention, to separate, in time, the mixing process of the two components from the extrusion process and, if a plastic cartridge is used, to extrude the cement dough with a conventional manually-driven extrusion device, such as is known, thus far, only for powder-liquid bone cements, e.g. the Palamix® cementing gun (Heraeus Medical GmbH). A specialised gas-driven cementing gun is not required.

The two components, A and B, are separate components and can be stored separately in their non-cured condition. Component A is a paste and, preferably, is tack-free already when it is in its storage condition. Component B is a powder and/or powder mixture and can therefore be manufactured easily and inexpensively. Since the radiopaquer is present in powdered component B, problems arising from sedimentation in pastes can be excluded.

The term, "comprise", as used in the present invention shall also include the meanings "to consist of" and "essentially consist of". Room temperature (RT) shall be understood to be a temperature of 23° C.

The particle size D50 shall be understood to be the volume average of the particle size. D50 is determined by means of a laser diffraction method using scattered light and the laser diffraction particle size analyzer LS 13320 made by Beckman Coulter, USA.

The number average molar mass is determined by means of gel permeation chromatography (GPC).

The bone cement according to the invention contains at least one hydroperoxide, at least one tertiary amine, at least one heavy metal salt, and at least one reducing agent distributed over the two components, as is illustrated in detail below. These four ingredients form a redox initiator system. The redox system is activated by the two components being mixed and then initiates, through radical formation, the polymerisation of the methylmethacrylate, upon which the bone cement cures.

The ingredients of the redox initiator system, i.e. hydroperoxide, tertiary amine, heavy metal salt, and reducing agent, are all soluble in methylmethacrylate at room temperature. The term, "soluble in methylmethacrylate", shall be understood to mean that a solution that is clear to the eye is formed. This is determined visually by eye.

Referring to the methylmethacrylate-insoluble particulate polymer that has a particle size D50 of less than 50 µm, the term, "methylmethacrylate-insoluble", shall be understood to mean that no solution that is clear to the eye is formed. This is determined visually by eye.

The paste used as component A comprises methylmethacrylate as monomer. Methylmethacrylate is also referred to as methacrylic acid methylester. Hereinafter, methylmethacrylate shall be abbreviated as MMA, as is commonly done. The weight fraction of MMA in component A can vary in broad ranges. Preferably, the weight fraction of MMA in component A is in the range of 30 to 50 wt. %.

The paste used as component A further comprises at least one methylmethacrylate-soluble polymer having a number average molar mass of less than 500,000 Dalton. The number average molar mass of the at least one methylmethacrylate-soluble polymer preferably is at least 100,000 Dalton.

As a matter of principle, all methylmethacrylate-soluble polymers can be used. One or more methylmethacrylate-soluble polymers can be used. The at least one methylmethacrylate-soluble polymer is essential for attaining the absence of tackiness of the pasty component A.

Examples of suitable polymers include polymethylmethacrylate and copolymers of methylmethacrylate and one or more monomers that can be copolymerised with it, such as methylacrylate, styrene, and ethylacrylate.

Particularly preferably, the methylmethacrylate-soluble polymer having a number average molar mass of less than 500,000 Dalton is selected from polymethylmethacrylate, poly(methylmethacrylate-co-methylacrylate), poly(methylmethacrylate-co-styrene), and mixtures thereof.

The weight fraction of the at least one methylmethacrylate-soluble polymer having a number average molar mass of less than 500,000 Dalton in component A can vary in broad ranges, whereby the weight fraction preferably is in the range of 12 to 30 wt. %.

The paste used as component A further comprises at least one methylmethacrylate-insoluble particulate polymer that has a particle size D50 of less than 50 µm. Preferably, the at least one methylmethacrylate-insoluble particulate polymer has a particle size D50 of at least 0.5 µm. The at least one methylmethacrylate-insoluble particulate polymer preferably has a particle size D50 in the range of 5 to 10 µm.

Preferably, the methylmethacrylate-insoluble particulate polymer has a density that differs only little from the density of methylmethacrylate. As a result, there is little or virtually no sedimentation of insoluble polymer particles in paste A evident.

As a matter of principle, all MMA-insoluble polymers can be used as methylmethacrylate-insoluble polymer particles having a particle size D50 of less than 50 µm. Examples of suitable polymers include cross-linked polymethylmethacrylate, cross-linked poly(methylmethacrylate-co-methacrylate), and cross-linked poly(methylmethacrylate-co-styrene).

Cross-linked polymethylmethacrylate and cross-linked poly(methylmethacrylate-co-methacrylate) are a copolymer of methylmethacrylate or a mixture of methylmethacrylate and methacrylate and one or more bifunctional, trifunctional and/or multi-functional monomers that can be copolymerised with it. Pertinent examples of said bifunctional, trifunctional and/or multi-functional monomers acting as cross-linkers include dimethacrylates, trimethacrylates, tetramethacrylates, diacrylates, triacrylates, tetraacrylates, whereby dimethacrylates are preferred.

Preferably, the methylmethacrylate-insoluble particulate polymer having a particle size D50 of less than 50 μm is cross-linked polymethylmethacrylate. Copolymers of methylmethacrylate and ethylene glycol dimethacrylate and copolymers of methylmethacrylate and propane-1,2-diol-dimethacrylate are particularly preferred.

The weight fraction of the at least one methylmethacrylate-insoluble particulate polymer having a particle size D50 of less than 50 μm in component A can vary in broad ranges, whereby the weight fraction preferably is in the range of 10 to 40 wt. %.

The paste used as component A further comprises at least one methylmethacrylate-soluble hydroperoxide. One or more methylmethacrylate-soluble hydroperoxides can be used. The hydroperoxide serves as radical initiator. Cumene hydroperoxide, t-butyl-hydroperoxide or isoamyl-hydroperoxide and mixtures thereof are preferred as methylmethacrylate-soluble hydroperoxide. Said hydroperoxides are characterised by their high temperature stability and storage stability.

The weight fraction of the at least one methylmethacrylate-soluble hydroperoxide in component A can vary in broad ranges, whereby the weight fraction preferably is in the range of 0.01 to 1.0 wt. %.

The paste used as component A further comprises at least one methylmethacrylate-soluble tertiary amine. One or more methylmethacrylate-soluble tertiary amines can be used. Preferred examples are tertiary aromatic amines. These contain at least one aromatic ring, in particular at least one benzene ring. The tertiary amine is preferred to be a toluidine and/or an aniline.

Particularly preferably, the tertiary amine is selected from one or more of N,N-dimethyl-o-toluidine, N,N-bis-hydroxyethyl-p-toluidine, and N,N-dimethyl-aniline.

The weight fraction of the at least one methylmethacrylate-soluble tertiary amine in component A can vary in broad ranges, whereby the weight fraction preferably is in the range of 0.4 to 4.0 wt. %.

Tertiary amines and hydroperoxides can be combined in pasty component A because the decomposition of the hydroperoxide requires not only tertiary amines, but also heavy metals salts and at least one reducing agent to be present.

In the scope of the invention, pasty component A can further contain, aside from the methylmethacrylate, one or more mono-functional or multi-functional monomers, if applicable, that can be copolymerised with methylmethacrylate. Pertinent examples include alkylacrylates, mono- and dicarboxylic acids having at least one olefinic group, dimethacrylates, methacrylamide, and 2-hydroxyethylmethacrylate (HEMA). Preferred examples include ethylene glycol dimethacrylate, propylene glycol dimethacrylate, butandiol-1,4-dimethacrylate, ethylmethacrylate, hydroxyethylmethacrylate, itaconic acid dimethylester, and methacrylamide. Provided said further monomers are indeed used, their weight fraction in component A is preferred to be no more than 5 wt. %.

Moreover, the paste as component A can contain further optional additives, e.g. one or more colourants and/or one or more pharmaceutical agents. Additives such as colourants and/or pharmaceutical agents can be present in pasty component A and/or powdered component B. Provided colourants and/or pharmaceutical agents are present in the bone cement according to the invention, these are preferred to be present in powdered component B.

The colourant preferably is a food dye or a coloured lacquer. Pertinent examples include E101, E104, E132, E141 (chlorophyllin), E142, riboflavin, lissamine green, and "Farblack Grün", which is the aluminium salt of a mixture of E104 and E132.

Pertinent examples of suitable pharmaceutical agents include antibiotics, antiphlogistics, steroids, hormones, growth factors, bisphosphonates, cytostatic agents, and gene vectors. Specific examples are given below in the description of component B.

The paste as component A can be subjected to a sterilisation, e.g. by means of a sterilising agent. The paste can be sterilised, e.g., using the sterilisation method described in EP 2596812 A1 through the action of β-propiolactone or the derivatives thereof. Besides, a sterilisation by hydrogen peroxide or hydrogen peroxide-releasing compounds, such as described, e.g., in DE 102009005534 B3, or by suitable peracids is feasible just as well.

In a preferred embodiment, the paste as component A consists, essentially or completely, just of methylmethacrylate, the at least one methylmethacrylate-soluble polymer, the at least one methylmethacrylate-insoluble particulate polymer, the at least one methylmethacrylate-soluble hydroperoxide, and the at least one methylmethacrylate-soluble tertiary amine, whereby sterilisation agent may be present in addition, if applicable.

The bone cement according to the invention further contains a powder and/or powder mixture as separate component B.

Powdered component B comprises at least one particulate radiopaquer having a particle size D50 of less than 50 μm. It can contain one or more radiopaquers, which are also referred to as X-ray contrast agent. It is customary to use radiopaquers in bone cements and they are commercially available.

The particulate radiopaquer having a particle size D50 of less than 50 μm can, e.g., be metal oxides, e.g. zirconium dioxide, barium sulfate, toxicologically non-objectionable heavy metal particles, e.g. tantalum, ferrite, and magnetite, or toxicologically non-objectionable calcium salts, e.g. $CaCO_3$, $CaSO_4$ or $CaSO_4 \cdot 2H_2O$, whereby zirconium dioxide and/or barium sulfate are preferred.

The weight fraction of the at least particulate radiopaquer having a particle size D50 of less than 50 μm in component B can vary in broad ranges, whereby the weight fraction preferably is in the range of 50 to 95 wt. %.

For radiographic visualisation of the polymethylmethacrylate cement it is necessary for the cement to contain at least one radiopaque substance. Radiopaquers, such as zirconium dioxide and barium sulfate, possess a high density. Whenever particles of high density are present in pastes, there is a risk of said particles sedimenting. According to the invention, the radiopaquers are present in powdered component B. For this reason, no radiopaquers need to be present in pasty component A. As a result, problems due to possible sedimentaton of the radiopaquers in pasty component A are excluded, as a matter of principle. Moreover, the radiopaquer particles act as support for the at least one methylmethacrylate-soluble heavy metal salt and also as support for the at least one methylmethacrylate-soluble reducing agent, which are also present in powdered component B.

Powdered component B further comprises at least one methylmethacrylate-soluble heavy metal salt. One or more heavy metal salts can be used. The heavy metal salt serves for radical formation. As a matter of principle, all common methylmethacrylate-soluble heavy metal salts can be used. Specifically, the methylmethacrylate-soluble heavy metal salt is one that has at least two oxidation states. Heavy metal salts include heavy metal complexes. Usually, the density of heavy metal salts at 20° C. is more than 5 g/cm$^3$.

Suitable heavy metal salts include, e.g., the salts of copper, cobalt, iron or manganese, whereby Co(II) and Cu(II) salts are particularly preferred. The heavy metal salts comprise, as anions, in particular organic ligands or organic complex ligands. Pertinent examples of suitable anions include alcoholate, acrylate, methacrylate, acetylacetonate, and 2-ethylhexanoate, whereby 2-ethylhexanoate is preferred.

Preferred examples of methylmethacrylate-soluble heavy metal salts include copper(II) 2-ethylhexanoate, copper(II) methacrylate, copper(II) bisacetylacetonate, cobalt(II) 2-ethylhexanoate, and cobalt(II) bisacetylacetonate.

The weight fraction of the at least one methylmethacrylate-soluble heavy metal salt in component B can vary in broad ranges, whereby the weight fraction preferably is in the range of 0.5 to 2.0 wt. %.

Powdered component B further comprises at least one methylmethacrylate-soluble reducing agent. One or more reducing agents can be used. All common reducing agents for this purpose can be used, such as, e.g., methylmethacrylate-soluble reductones and/or endiols or imides.

Saccharine, phthalimide, succinimide, maleimide, palmitoylascorbic acid, and benzoin are suitable, e.g., as methylmethacrylate-soluble reducing agents. Saccharine is particularly preferred since this inexpensive reducing agent is used widely as a sweetener (E 954) and is toxicologically non-objectionable in as far as is currently known.

The weight fraction of the at least one methylmethacrylate-soluble reducing agent in component B can vary in broad ranges, whereby the weight fraction preferably is in the range of 2 to 28 wt. %.

In a preferred embodiment, powdered component B further contains silicon dioxide. In this context, silicon dioxide shall also include mixed oxides made up of silicon dioxide and one or more other metal oxides. Said mixed oxides also comprise superficial silanol groups capable of forming hydrogen bridge bonds. The weight fraction of silicon dioxide in component B can vary in broad ranges and preferably is 0.1 to 20 wt. %. The silicon dioxide preferably has a BET surface of at least 40 m$^2$/g, more preferably of 40 to 450 m$^2$/g, particularly preferably of 40 to 380 m$^2$/g. Pyrogenic silicic acids, in particular highly disperse pyrogenic silicic acids, e.g. the Aerosils® of Evonik, Germany, e.g. AEROSIL® 380, are preferred.

Due to the use of silicon dioxide, paste A can advantageously be set to have a low viscosity and a thixotropic cement dough showing thixotropic behaviour upon shearing can be formed after mixing with powdered component B.

Moreover, powdered component B can advantageously further contain one or more optional additives, e.g. one or more colourants and/or one or more pharmaceutical agents, such as, e.g., anti-infective agents, antiseptics, antiphlogistics, bisphosphonates, growth factors, antibiotics, steroids, hormones, cytostatic agents, and gene vectors.

The colourant is, e.g., colour pigments, food dyes or coloured lacquers. Pertinent examples include E101, E104, E132, E141 (chlorophyllin), E142, riboflavin, lissamine green, and "Farblack Grün", which is the aluminium salt of a mixture of E104 and E132.

Pharmaceutical agents, in particular anti-infective agents, antiseptics, antiphlogistics, bisphosphonates, and growth factors, can be stored with relatively little difficulty for an extended period of time in the dry powder mixture of component B. Specifically, gentamicin, tobramycin, clindamycin, vancomycin, teicoplanin, daptomycin, and fosfomycin, which can be used in the form of easily water-soluble salts or also in the form of poorly water-soluble salts or complexes, are preferred as anti-infective agents. Specifically, octenidine dihydrochloride, polyhexanide, calcium peroxide, and carbamide peroxide, are conceivable as antiseptics.

Since the additives can be present in dry, non-dissolved condition in component B, stability problems and therefore storability problems can be largely prevented as compared to being taken up in pasty components of bone cements, in particular those containing monomers.

Powdered component B can be sterilised in known manner through the action of gamma radiation or ethylene oxide.

In a preferred embodiment, pasty component A of the two-component bone cement comprises, relative to the total weight of component A, a1) 30 to 50 wt. % methylmethacrylate;
a2) 12 to 30 wt. % of at least one methylmethacrylate-soluble polymer having a number average molar mass of less than 500,000 Dalton;
a3) 10 to 40 wt. % of at least one methylmethacrylate-insoluble particulate polymer having a particle size D50 of less than 50 µm;
a4) 0.01 to 1.0 wt. % of at least one methylmethacrylate-soluble hydroperoxide; and
a5) 0.4 to 4.0 wt. % of at least one methylmethacrylate-soluble tertiary amine.

In a preferred embodiment, powdered component B of the two-component bone cement comprises, relative to the total weight of component B, b1) 50 to 95 wt. % of at least one particulate radiopaquer having a particle size D50 of less than 50 µm;
b2) 0.5 to 2.0 wt. % of at least one methylmethacrylate-soluble heavy metal salt; and
b3) 2 to 28 wt. % of at least one methylmethacrylate-soluble reducing agent; and, if applicable,
b4) 2 to 45 wt. % of at least one pharmaceutical agent;

whereby the fraction of component b1) is preferred to be 70 to 95 wt. %, provided component B contains no pharmaceutical agent.

In a particularly preferred embodiment, pasty component A and powdered component B contain said ingredients in amounts that correspond to the quantitative fractions specified above. The quantity of radiopaquer in component B can vary relatively widely, depending on whether a pharmaceutical agent is present also.

The invention also relates to a method for producing a cured cement using the two-component bone cement according to the invention, which comprises mixing pasty component A and powdered component B to form a self-curing cement dough. The two components are preferably mixed at a weight ratio of 80 to 90 parts by weight of paste A to 5 to 10 parts by weight of powder B.

The mixing process of the two components can be separated in time from the extrusion process. The two components can be mixed, e.g. in a cartridge, such as a plastic cartridge, and the cement dough thus formed can be extruded using an extrusion device. Suitable for this purpose are, e.g., conventional manually-driven extrusion devices that are also used with conventional powder-liquid bone cements, e.g. the Palamix® cementing gun made by Heraeus Medical GmbH.

After mixing paste A and powdered component B, a tack-free plastically deformable cement dough is generated immediately, without any waiting time, that self-cures by means of radical polymerisation.

The polymethylmethacrylate bone cement according to the invention and/or the cement dough obtained after mixing components A and B is particularly well-suited, e.g., for mechanical fixation of articular endoprostheses, for producing temporary spacers, for vertebroplasty, for kyphoplasty, and for producing active substance supports for local active substance release.

The invention shall be illustrated in more detail by the following examples without limiting the invention in any way or form.

EXAMPLES

Production of a Paste A for Examples 1-3

A paste A of the following composition was produced for each of examples 1-3:

| | |
|---|---|
| 36.25 g | methylmethacrylate |
| 0.40 g | methacrylamide |
| 0.30 g | 2-hydroxyethylmethacrylate |
| 0.90 g | N,N-dimethyl-p-toluidine |
| 2.10 g | bis(2-hydroxyethyl)-p-toluidine |
| 0.10 g | 80% cumene hydroperoxide solution |
| 0.03 g | 2,6-di-t-butyl-4-methyl-phenol |
| 19.40 g | poly(methylmethacrylate-co-methylacrylate) Mn < 500,000 Dalton |
| 19.40 g | MMA-insoluble, ethylene glycol dimethacrylate-crosslinked polymethylmethacrylate having a particle size D50 of less than 50 μm. |

All substances were procured from Sigma-Aldrich with the exception of the soluble polymethylmethacrylate-co-methacrylate and the insoluble polymethylmethacrylate. The components were weighed into a plastic cup, stirred vigorously, and, after closing the cup with a screw lid, left for at least 18 hours at room temperature.

Production of a Powdered Component B for Example 1

Composition of Powdered Component B:

| | |
|---|---|
| 4.80 g | zirconium dioxide |
| 0.06 g | copper(II) 2-ethylhexanoate |
| 0.05 g | "Grünlack" (coloured aluminium lacquer made of indigo disulfonic acid and quinoline yellow) |
| 0.60 g | saccharine |
| 1.18 g | gentamicin sulfate |

With the exception of gentamicin sulfate, all substances of component B were procured from Sigma-Aldrich. Gentamicin sulfate from Fujian Fukang Ltd. (PR China) was used.

Production of a Powdered Component B for Example 2

Composition of Powdered Component B:

| | |
|---|---|
| 4.80 g | zirconium dioxide |
| 0.06 g | copper(II) 2-ethylhexanoate |
| 0.05 g | "Grünlack" (coloured aluminium lacquer made of indigo disulfonic acid and quinoline yellow) |
| 0.60 g | saccharine |
| 1.00 g | vancomycin hydrochloride |

With the exception of vancomycin hydrochloride, all substances of component B were procured from Sigma-Aldrich. The vancomycin hydrochloride was from Axellia Pharmaceuticals (Denmark).

Production of a Powdered Component B for Example 3

Composition of Powdered Component B:

| | |
|---|---|
| 4.80 g | zirconium dioxide |
| 0.06 g | copper(II) 2-ethylhexanoate |
| 0.05 g | "Grünlack" (coloured aluminium lacquer made of indigo disulfonic acid and quinoline yellow) |
| 0.60 g | saccharine |

Examples 1 to 3

Mixing and Application

Paste A for examples 1-3 and powdered component B of examples 1 to 3 were placed together and stirred vigorously, whereby the entire quantity of the powder and paste specified above were used. A green, tack-free cement dough was thus produced immediately in all examples. Said cement dough was transferred into the cartridge of the Palamix® cementing system and was extruded through the usual dispensing tube of the cementing system without any difficulty using the manually-operated Palamix® cementing gun.

Production of Test Bodies

ISO 5833 requires a flexural strength of ≥50 MPa, a flexural modulus of ≥1,800 MPa, and a compressive strength of ≥70 MPa. Test bodies were produced for the test of the mechanical properties of the paste cements of examples 1-3 in accordance with ISO 5833. Paste A for examples 1-3 and powdered component B of examples 1-3 were placed together and stirred vigorously, whereby the entire quantity of the powder and paste specified above were used. A green, tack-free cement dough that cured by exothermic reaction after just a few minutes was thus produced immediately in all examples.

The cement dough of examples 1-3 was used to produce strip-shaped test bodies sized 75 mm×10 mm×3.3 mm for the test of the flexural strength and flexural modulus in accordance with ISO 5833. In addition, cylindrical test bodies (diameter 6 mm, height 12 mm) were produced for the compressive strength test.

After storage of the test bodies at 23° C. and a relative humidity of 50% for a period of 24 hours, the flexural strength, flexural modulus, and the compressive strength were determined in accordance with ISO 5833. The results show that the mechanical requirements of ISO 5833 with regard to the flexural strength, flexural modulus, and the compressive strength were met by the cements of examples 1-3.

| Example | Flexural strength [MPa] | Flexural modulus [MPa] | Compressive strength [MPa] |
|---|---|---|---|
| 1 | 64.5 ± 2.4 | 2655 ± 59 | 100.4 ± 1.3 |
| 2 | 61.9 ± 2.4 | 2538 ± 97 | 99.8 ± 1.8 |
| 3 | 66.2 ± 1.0 | 2575 ± 67 | 96.5 ± 0.9 |

Examples 4 to 6

Pasty component A was produced in the same manner as in examples 1-3 with the exception of 0.1 wt. % propiolactone having been added. The powdered components B had the same composition as in examples 1-3. Three weeks after preparation and storage at room temperature, pasty component A was manually mixed with each of the powdered components B of examples 1-3, whereby the entire quantity of the powder and paste specified above were used, in order to obtain the cement dough of examples 4-6. Similar to examples 1-3, a tack-free cement dough was produced that self-cured by exothermic reaction after approx. 4 minutes.

Example 7

Composition of Paste A:

| | |
|---|---|
| 36.25 g | methylmethacrylate |
| 0.40 g | methacrylamide |
| 0.30 g | 2-hydroxyethylmethacrylate |
| 0.90 g | N,N-dimethyl-p-toluidine |
| 2.10 g | bis(2-hydroxyethyl)-p-toluidine |
| 0.10 g | 80% cumene hydroperoxide solution |
| 0.03 g | 2,6-di-t-butyl-4-methyl-phenol |
| 15.40 g | poly(methylmethacrylate-co-methylacrylate) Mn < 500,000 Dalton |
| 19.40 g | MMA-insoluble, ethylene glycol dimethacrylate-crosslinked polymethylmethacrylate having a particle size D50 of less than 50 µm. |

Composition of Powdered Component B:

| | |
|---|---|
| 4.80 g | zirconium dioxide |
| 0.70 g | Aerosil ® 380 (pyrogenic silicic acid) |
| 0.06 g | copper(II) 2-ethylhexanoate |
| 0.05 g | "Grünlack" (coloured aluminium lacquer made of indigo disulfonic acid and quinoline yellow) |
| 0.60 g | saccharine |
| 1.18 g | gentamicin sulfate |

It was easily possible to mix paste A and component B, whereby the entire quantity of the powder and paste specified above were used. The cement dough was tack-free and easy to deform plastically upon shearing. It was possible to process the cement dough for approx. 4 minutes, after which it self-cured by exothermic reaction.

The invention claimed is:

1. Two-component bone cement, comprising
   A) a paste as component A, comprising
      a1) methylmethacrylate;
      a2) at least one polymer having a number average molar mass of less than 500,000 Dalton selected from the group consisting of polymethylmethacrylate, poly(methylmethacrylate-co-methylacrylate), and poly(methylmethacrylate-co-styrene);
      a3) at least one cross-linked polymethylmethacrylate particulate polymer having a particle size D50 of less than 50 µm;
      a4) at least one hydroperoxide selected from the group consisting of cumene hydroperoxide, tert.-butyl-hydroperoxide, and isoamyl-hydroperoxide; and
      a5) at least one methylmethacrylate-soluble tertiary amine selected from the group consisting of N,N-dimethyl-o-toluidine, N,N-bis-hydroxyethyl-p-toluidine, and N,N-dimethylaniline;
   and
   B) a powder as component B, comprising
      b1) at least one particulate radiopaquer selected from the group consisting of zirconium dioxide and barium sulfate having a particle size D50 of less than 50 µm;
      b2) at least one heavy metal salt selected from the group consisting of copper(II) 2-ethylhexanoate, copper(II) methacrylate, copper(II) bisacetylacetonate, cobalt(II) 2-ethyl hexanoate, and cobalt(II) bisacetylacetonate; and
      b3) at least one reducing agent selected from the group consisting of saccharine, phthalimide, succinimide, maleimide, palmitovlascorbic acid, and benzoin.

2. Two-component bone cement according to claim 1, wherein pasty component A comprises
   a1) 30 to 50 wt. % methylmethacrylate;
   a2) 12 to 30 wt. % of said at least one polymer having a number average molar mass of less than 500,000 Dalton;
   a3) 10 to 40 wt. % of at said least one particulate polymer having a particle size D50 of less than 50 µm;
   a4) 0.01 to 1.0 wt. % of said at least one hydroperoxide; and
   a5) 0.4 to 4.0 wt. % of said at least one tertiary amine.

3. Two-component bone cement according to claim 1, wherein powdered component B comprises
   b1) 50 to 95 wt. % of said at least one particulate radiopaquer having a particle size D50 of less than 50 µm;
   b2) 0.5 to 2.0 wt. % of said at least one heavy metal salt; and
   b3) 2 to 28 wt. % of said at least one reducing agent.

4. Two-component bone cement according to claim 1, wherein powdered component B further comprises
   b4) at least one pharmaceutical agent.

5. Two-component bone cement according to claim 1, wherein the powdered component B contains 0.1 to 20 wt. % silicon dioxide that has a BET surface of at least 40 $m^2/g$.

6. Two-component bone cement according to claim 1, wherein the mixing ratio of the two components is 80 to 90 parts by weight of pasty component A to 5 to 10 parts by weight of powdered component B.

7. Two-component bone cement according to claim 1, wherein powdered component B further comprises at least one additive selected from the group consisting of colorants, anti-infective agents, antiseptics, antiphlogistics, bisphosphonates, and growth factors.

8. Method for mechanical fixation of articular endoprostheses, for producing temporary spacers, for vertebroplasty, for kyphoplasty or for producing active substance supports for local active substance release with the two-component bone cement of claim 1.

9. Method for producing a cured cement using a two-component bone cement of claim 1, comprising the mixing of pasty component A and powdered component B in order to obtain a self-curing cement dough.

* * * * *